(12) United States Patent
Rizk

(10) Patent No.: US 11,521,707 B2
(45) Date of Patent: Dec. 6, 2022

(54) SOFTWARE ACCELERATED GENOMIC READ MAPPING

(71) Applicant: Illumina, Inc., San Diego, CA (US)

(72) Inventor: Guillaume Alexandre Pascal Rizk, Rennes (FR)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 17/476,456

(22) Filed: Sep. 15, 2021

(65) Prior Publication Data

US 2022/0084625 A1  Mar. 17, 2022

Related U.S. Application Data

(60) Provisional application No. 63/078,890, filed on Sep. 15, 2020.

(51) Int. Cl.
*G16B 20/00* (2019.01)

(52) U.S. Cl.
CPC .................................. *G16B 20/00* (2019.02)

(58) Field of Classification Search
CPC ........ G16B 30/10; G16B 30/00; G16B 50/30; G16B 30/20; G16B 50/00; G16B 40/00; G16B 50/50; G16B 45/00; G16B 40/20; G16B 20/20; G16B 20/40; G16B 50/10; G16B 50/40; G06F 16/2255; G06F 16/24578; G06F 9/505; G06F 9/5055; G06F 16/20; G06F 16/137; G06F 16/22;
(Continued)

(56) References Cited

U.S. PATENT DOCUMENTS

| 9,449,191 | B2 | 9/2016 | McCarthy et al. |
| 9,942,206 | B1 | 4/2018 | Miller et al. |
| 10,068,183 | B1 | 9/2018 | van Rooyen |

(Continued)

FOREIGN PATENT DOCUMENTS

| WO | WO2011/073680 A1 | 4/2020 | |
| WO | WO-2021055972 A1 * | 3/2021 | ............. G16B 30/10 |

OTHER PUBLICATIONS

Bingmann, T. et al. COBS: a compact bit-sliced signature index. IN Brisaboa and Puglisi (eds) SPIRE 2019, LCNS 11811, Springer Nature, Switzerland, p. 285-303. (Year: 2019).*

(Continued)

*Primary Examiner* — Mary K Zeman
(74) *Attorney, Agent, or Firm* — Fish & Richardson, P.C.

(57) ABSTRACT

Methods, systems, apparatus, and computer programs are disclosed for software-accelerated genomic data read mapping. In one aspect, the methods can include actions of obtaining a k-mer seed from a genomic data read, generating a genomic signature based on the obtained k-mer seed, determining a reference sequence location that match at least a portion of the k-mer seed using a hash data structure, wherein the hash data structure comprises N data cells comprising a first portion storing a predetermined genomic signature and a second portion storing a value that corresponds to a first occurrence of a reference sequence location that match at least a portion of the k-mer seed from which the predetermined genomic signature was derived, and selecting the determined reference sequence location as an actual alignment for the obtained k-mer seed based on one or more alignment scores.

20 Claims, 5 Drawing Sheets

(58) Field of Classification Search
CPC ..... G06F 16/2264; C12Q 1/6869; C12Q 1/68; G06K 19/06037; G06N 5/025; G16H 10/00
See application file for complete search history.

(56) References Cited

U.S. PATENT DOCUMENTS

| | | | |
|---|---|---|---|
| 10,192,029 B2 | 1/2019 | Wang et al. | |
| 10,673,826 B2 | 6/2020 | Sinclair et al. | |
| 2009/0024555 A1* | 1/2009 | Rieck | G06K 9/6201 706/54 |
| 2015/0294065 A1* | 10/2015 | Gautier | G16B 30/10 702/19 |
| 2016/0019339 A1* | 1/2016 | Sazonov | G16B 30/20 702/20 |
| 2017/0147597 A1* | 5/2017 | Leighton | G16B 30/10 |
| 2020/0005898 A1* | 1/2020 | Carrera Perez | G16B 20/00 |

OTHER PUBLICATIONS

Deorowicz, S. et al. KMC-2: fast and resource-frugal k-mer counting. Bioinformatics 31:10, 1569-1576. 2015 (Year: 2015).*
Ju, C. J-T. et al. TachoRoll: an efficient approach for Signature Profiling in Genomic Data through Variable—Length k-mers. BioRxiv, Dec. 6, 2017, 18 pages. doi: doi.org/10.1101/229708. (Year: 2017).*
Petrucci, E. et al. Iterative spaced seed hashing: closing the gap between spaced seed hashing and k-mer hashing.(2020) Journal of Computational Biology, 27:2 p. 223-233. (Year: 2020).*
Girotto et al. (2018) Efficient computation of spaced seed hashing with block indexing. BMC Bioinformatics 19:Suppl 15) 441, 10 pages. (Year: 2018).*
Marchet et al. (2020) REINDEER: an efficient indexing of k-mer presence and abundance in sequencing datasets. Bioinformatics 36:i77-i85. (Year: 2020).*
DSK: k-mer counting with very low memory usage, Bioinformatics, vol. 29 No. 5 2013, pp. 652-653.
Illumina DRAGEN Bio-IT Platform v3.5, User Guide, 2020 Illumina, Inc. pp. 1-158.
Ge et al., "FusionMap: detecting fusion genes from next-generation sequencing data at base-pair resolution," Bioinformatics, Jul. 15, 2011, 27(14):1922-8.
Manekar et al., "A benchmark study of k-mer counting methods for high-throughput sequencing," GigaScience, Dec. 2018, 7(12):giy125.
Mcvicar et al., "K-mer counting using Bloom filters with an FPGA-attached HMC," 2017 IEEE 25th Annual International Symposium on Field-Programmable Custom Computing Machines (FCCM), Apr. 30, 2017, 203-10.
Mohamadi et al., "ntHash: recursive nucleotide hashing," Bioinformatics, Nov. 15, 2016, 32(22):3492-4.
Pan et al., "Optimizing high performance distributed memory parallel hash tables for DNA k-mer counting," SC18: International Conference for High Performance Computing, Networking, Storage and Analysis, Nov. 11, 2018, 135-47.
PCT International Search Report and Written Opinion in International Appln. No. PCT/US2021/050557, dated Jan. 24, 2022, 20 pages.
Wu et al., "Fast and SNP-tolerant detection of complex variants and splicing in short reads," Bioinformatics, Apr. 1, 2010, 26(7):873-81.
Wu, "Bitpacking techniques for indexing genomes: II. Enhanced suffix arrays," Algorithms for Molecular Biology, Dec. 2016, 11(1):1-6.

* cited by examiner

SOFTWARE ACCELERATED GENOMIC READ MAPPING

BACKGROUND

This application claims priority to U.S. Application Ser. No. 63/078,890, filed on Sep. 15, 2020, which is incorporated by reference in its entirety.

BACKGROUND

In some cases, genomic read mapping describes a method to identify the locus of a gene and the distances between genes. Computers can be used to analyze one or more sets of genomic data and correlate a collection of molecular markers, such as a series of nucleotides, with their respective positions on a given reference genome. In this way, a computer can be used to "map" the collection of molecular markers onto the reference genome.

SUMMARY

The present disclosure is directed towards methods, systems, and computer programs for software-accelerated genomic read mapping. In one aspect, the present disclosure relates to the generation of a hash table that facilitates software-accelerated genomic read mapping. The hash table can include data representing a reference genome that is indexed using genomic data signatures. In some implementations, the generated hash table can be used to determine a mapping between a received genomic read and the reference genome.

According to one innovative aspect of the present disclosure, a method for software-accelerated genomic data read mapping is disclosed. In one aspect, the method can include actions of obtaining, by one or more computers, a k-mer seed from a genomic data read, generating, by the one or more computers, a genomic signature based on the obtained k-mer seed, determining, by one or more computers, a reference sequence location that match at least a portion of the k-mer seed using a hash data structure, wherein the hash data structure comprises N data cells comprising a first portion storing a predetermined genomic signature and a second portion storing a value that corresponds to a first occurrence of a reference sequence location that match at least a portion of the k-mer seed from which the predetermined genomic signature was derived, and selecting, by one or more computers, the determined reference sequence location as an actual alignment for the obtained k-mer seed based on one or more alignment scores.

Other versions include corresponding systems, apparatus, and computer programs that have been configured to perform the actions of the aforementioned methods.

These and other versions may optionally include one or more of the following features. For instance, in some implementations, the predetermined genomic signature can occupy only one byte of memory storage.

In some implementations, the value can occupy only four bytes of memory storage.

In some implementations, the hash data structure is a single array of N data cells.

In some implementations, the method can further include filtering, by one or more computers, the genomic data read based on a first set of values corresponding to one or more k-mer seeds of the genomic data read.

In some implementations, the first set of values can include a result of a predetermined operation applied to the one or more k-mer seeds of the genomic data read, and wherein the first set of values is used to obtain the k-mer seed from the genomic data read.

In some implementations, the predetermined operation can include generating a hash value based on the one or more k-mer seeds of the genomic data read and a hash function.

In some implementations, determining the reference sequence locations can include computing, by one or more computers, a first position for the k-mer seed of the genomic data read, wherein the first position corresponds to a location of the k-mer seed within the genomic data read, and computing, by one or more computers, a second position for the k-mer seed, wherein the second position corresponds to a location of the k-mer seed within the reference genomic data, and wherein the second position is computed based on the hash data structure.

In some implementations, the method can further include sorting, by one or more computers, the one or more reference sequence locations based on the hash data structure and the genomic data read.

In some implementations, the method can further include generating, by one or more computers, the one or more alignment scores based on sorting the one or more reference sequence locations.

In some implementations, the method can further include selecting at least one of the determined reference sequence locations as the actual alignment for the obtained k-mer seed comprises comparing the one or more alignment scores to a threshold value.

In some implementations, the method can further include the one or more alignment scores comprises a numerical value representing a number of mismatches between the obtained k-mer seed from the genomic data read and the reference sequence location.

In some implementations, each subsequent occurrences of a reference sequence location that matches at least a portion of the k-mer seed from which the predetermined genomic signature was derived after first occurrence is discarded.

According to another innovative aspect of the present disclosure, a method for generating a hash table for software-accelerated genomic data read mapping is disclosed. In one aspect, the method can include actions of receiving, by one or more computers, genomic data, wherein the genomic data is derived from parent genomic data, generating, by the one or more computers, a first set of values based on the genomic data, generating, by one or more computers, a subset of the genomic data based on the first set of values, computing, by one or more computers, a signature for each k-mer of the subset of the genomic data, wherein the signature is computed based on a first hash function, computing, by one or more computers, a first attribute for each k-mer of the subset of the genomic data, wherein the first attribute comprises a position of a given k-mer of the genomic data within a sequence of the genomic data, computing, by one or more computers, an index for each k-mer of the subset of the genomic data, wherein the index is computed based on a second hash function, and storing, by one or more computers, the signature and the first attribute for each k-mer of the subset of the genomic data within a hash data structure based on the index for each k-mer of the subset of the genomic data.

Other versions include corresponding systems, apparatus, and computer programs that have been configured to perform the actions of the aforementioned methods.

These and other versions may optionally include one or more of the following features. For instance, in some implementations, each k-mer of the subset of the genomic data is a k-mer that includes k letters representing a string of one or more nucleotides.

In some implementations, the first set of values can include a representation of a number of times that a given k-mer of the genomic data occurs within the parent genomic data.

In some implementations, the first set of values comprises a representation of a hash value computed based on a corresponding k-mer of the genomic data.

In some implementations, a memory allocation size used to store the signature for a given k-mer of the subset is smaller than a memory allocation size used to store the given k-mer.

In some implementations, the method can further include sending, by the one or more computers, data corresponding to the hash data structure as a data package to a first device.

In some implementations, the first device is a memory storage device.

In some implementations, a second device reads the data corresponding to the hash data structure from the first device. In such implementations, the second device can perform a series of operations to generate a second hash data structure based on the data corresponding to the hash data structure.

A seed as used herein generally refers to a series of base calls or nucleotides identified, obtained, or extracted from a genomic data read.

A k-mer, also referred to herein as a k-mer seed, is a sequence of elements, such as base calls or nucleotides, where the number of elements, e.g., base calls or nucleotides, in the sequence for a given k-mer is defined by "k".

A genomic data read generally includes data generated by a nucleic acid sequencer that corresponds to base calls or nucleotides of a portion of a sample genome sequenced by the nucleic acid sequencer.

A genomic signature, also referred to herein as a signature, is or includes data that identifies a hash table location, e.g., a bucket, slot, or cell. Such data can also be referred to as a hash key, e.g., a genomic hash key. A signature is a genomic signature if it is generated from or points to a location identifying genomic data.

A reference sequence location refers to a particular site or portion of a reference sequence, e.g., a reference nucleic acid sequence.

A hash data structure stores data in an associative manner and can include a data structure that maps a hash key to a memory location, bucket, or cell using a hash function.

An alignment score is or includes data that indicates a confidence level that a genomic data read or k-mer seed that is mapped to a particular reference sequence actually corresponds to that particular reference sequence location.

Genomic data can include any data that relates to a genome of a subject, e.g., a human subject.

Parent genomic data can include any superset of genomic data from which a subset of genomic data is extracted. For example, a genomic data read can be an example of parent genomic from which a k-mer seed can be extracted.

A value "based on" certain genomic data is a value that is derived from that genomic data.

A first hash function can include an initial occurrence of a hash function when multiple hash functions are used. Use of the term first hash function does not mean that the first hash function is different than any subsequent hash function that is used, but can be different.

An index is any data that can be used to identify a storage location of other data.

A second hash function can include a subsequent occurrence of a hash function when multiple hash functions are used. Use of the term second hash function does not mean that the second hash function is different than any prior has function that was previously used, but can be different.

The generated hash tables as described herein, and their use, can provide a number of technological benefits. Technological benefits can include a software-accelerated genomic read mapping algorithm that is faster and requires less memory and storage requirements than conventional methods. These benefits can be achieved, based at least in part, on the encoding of genomic reads into one-byte genomic data signatures for use as hash keys and use of a single array hash table. Other advantages of the present disclosure are also achieved through a number of filtering stages that help to reduce a number of reference locations under consideration.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
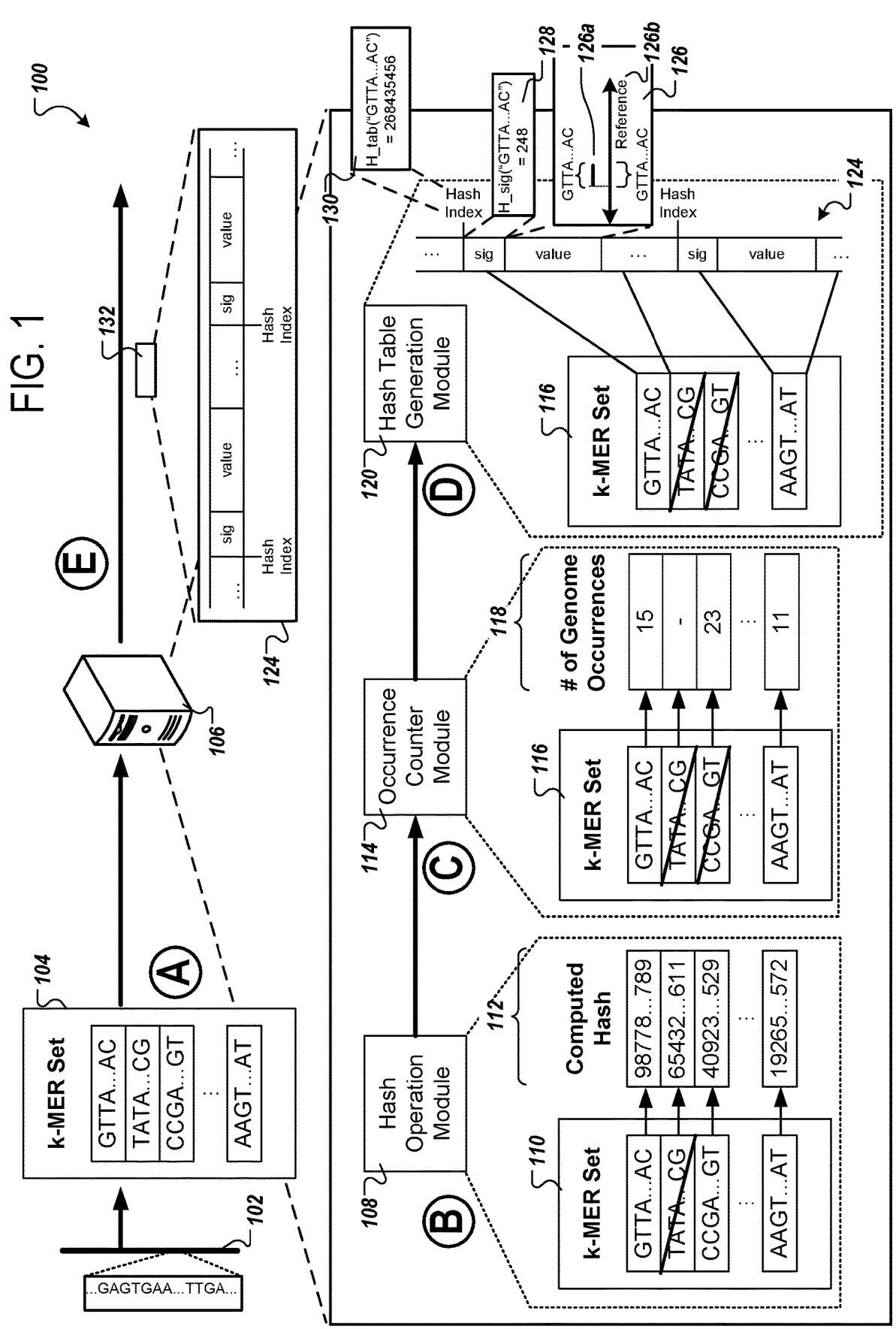
FIG. 1 is a diagram showing an example of a system for generating a hash table for software accelerated genomic read mapping.

The present disclosure is directed towards methods, systems, and computer programs for software-accelerated genomic read mapping. In one aspect, the present disclosure relates to the generation of a hash table that facilitates software-accelerated genomic read mapping. The hash table can include data representing a reference genome that is indexed using genomic data signatures. The generated hash table can then be used to determine a mapping between a received genomic read and the reference genome. The generated hash table, and its use, provides a number of technological benefits including a software-accelerated genomic read mapping algorithm that is faster and requires less memory and storage requirements than prior methods. These benefits can be achieved, based at least in part, on the encoding of genomic reads into one-byte genomic data signatures for use as hash keys and use of a single array hash table. Other advantages of the present disclosure are achieved through a number of filtering stages that help to reduce a number of reference locations under consideration.

In some implementations, the aspects of the present disclosure can be used to improve the performance of a reference-based genomic data compression algorithm. For example, the present disclosure can be used within reference based fastq compression. However, the present disclosure is not so limited. Instead, the software-accelerated genomic read mapper can be used in a number of other operations such as during generation of mapped and aligned genomic reads for input into a variant caller or during generation of mapped and aligned genomic reads for input into one or more stages of tertiary analysis.

In some implementations such as during use in a reference-based compression algorithm, the software-accelerated genomic read mapper can be configured to favor an increase in mapping speed while compromising a level of accuracy. However, in other implementations, the software-accelerated genomic read mapper can be configured to provide more accurate mapping at the expense of mapping speed. In general, variables and other parameters can be altered or optimized based on a given implementation as described herein, to provide a more accurate result, or to present a result more rapidly.

In some implementations, one or more filtering stages can be used to apply one or more different types of respective filters to generate the subset of the reference genomic data that will be used to generate the hash table. The filtered subset of reference genomic data can be generated to reduce memory usage and speed up computation. The filtered subset of the reference genomic data can then be stored in the hash table.

Software-accelerated genomic read mapping can be achieved using a computer that receives a genomic read and then queries the generated hash table to find locations in the reference genomic data that correspond to a given k-mer of the genomic read. The hash table facilitates software-accelerated genomic read mapping, because the hash table is configured to (i) reduce the memory used to store genomic signatures as hash keys and corresponding cells or buckets of references sequence locations that match the genomic signatures and (ii) be structured using a single array. The systems, methods, and features described herein can be used to determine one or more candidate alignments based, at least in part, on the generated hash table and process the candidate alignments to quickly find an alignment satisfying a given criteria.

FIG. 1 is a diagram showing an example of a system 100 for generating a hash table for software accelerated genomic read mapping. The system 100 includes a computer 106, a hash operation module 108, an occurrence counter module 114, and a hash table generation module 120. The computer 106 is configured to provide data to and receive data from the hash operation module 108, the occurrence counter module 114, and the hash table generation module 120. In some implementations, the computer 106 hosts one or more of the hash operation module 108, the occurrence counter module 114, and the hash table generation module 120 such that processing operations of the one or more modules can be processed locally on the computer 106. In other implementations, one or more of the hash operation module 108, the occurrence counter module 114, and the hash table generation module 120 can be hosted by one or more other computers that are connected to the computer 106.

The hash operation module 108 can generate one or more hash values corresponding to genomic data. In some cases, the genomic data can include nucleotide sequences in the form of k-mers. The occurrence counter module 114 can count a number of occurrences of a given form of genomic data within parent genomic data on which the genomic data is based. This is because, for example, a given k-mer can appear at a number of locations along the read sequence of nucleotides. The number of times a string of sequential nucleotides represented by the k-mer occurs within the read sequence of nucleotides may be obtained by the occurrence counter module 114. The hash table generation module 120 can then generate a hash table corresponding to the genomic data processed by the hash operation module 108 and the occurrence counter module 114. The example of FIG. 1 is described below in stages from stage A to stage E.

Within this specification, a given k-mer is defined as a sequence of sequential nucleotides where the number of nucleotides in the sequence for a given k-mer is defined by "k" and the nucleotides (or, more generally, bases) are represented by strings of letters from a defined vocabulary. For example, a given k-mer may represent the sequence "ATGCG" where the symbols: {A, C, G, T} represent the four types of nucleotides present in deoxyribonucleic acid (DNA), namely Adenine, Cytosine, Guanine, and Thymine. In ribonucleic acid (RNA), Thymine is replaced by Uracil (U).

The genomic data referred to in the present disclosure can include, for example, and not as a limitation, nucleotide sequences, Deoxyribonucleic acid (DNA) sequences, or Ribonucleic acid (RNA).

In stage A of the example of FIG. 1, the k-mer set 104, based on genomic data 102, is sent to the computer 106. In this example, the genomic data 102 can include a reference genome (which may also be referred to herein as a reference sequence) such as a DNA sequence assembled for an organism by one or more scientists and each k-mer in the k-mer set 104 corresponds to a particular sequence subset present in the genomic data 102 having a nucleotide length of k, where k is any positive integer greater than 0. For example, a k-mer AAGT . . . AT of the k-mer set 104 corresponds to a genomic data read, or a portion thereof, having a nucleotide sequence of length k nucleotides "AAGT . . . AT". The genomic data 102 includes at least one instance of the k-mer AAGT . . . AT meaning that the sequence of the k-mer AAGT . . . AT defined as a string of nucleotides corresponding to "AAGT . . . AT" occurs at least once within the nucleotide sequence corresponding to the genomic data 102. In some implementations, a reference sequence consists of a synthetic sequence conceived, at least in part, to improve the compressibility of the reads in view of further processing.

In some implementations, the k-mers within the k-mer set 104 can have a k-mer length of 16 nucleotides. However, the present disclosure is not limited to implementations using k-mers having a k-mer length of 16 nucleotides. In general, any number of nucleotides may be used for a given k-mer of a k-mer set. In some implementations, shorter seeds will have higher occurrence counts on the reference genome and may lead to higher computation time. Short seeds may also lead to high sensitivity. The seed length corresponding to the number of nucleotides within a k-mer of the k-mer set 104 may be adjusted for optimization purposes such as performance optimization.

The computer 106 receives the k-mer set 104. Depending on implementation, the computer 106 may communicate with one or more other computers to receive the k-mer set 104. For example, a pre-processing computer or other device may process the genomic data 102 and generate the k-mer set 104. The pre-processing computer or the other device may then communicate over a suitable communication network with the computer 106. The pre-processing computer of the other device may send the k-mer set 104 to the computer 106. In some implementations, the computer 106 performs operations of the pre-processing computer or the other device. For example, the computer 106 can receive the genomic data 102 and generate the k-mer set 104 based on the genomic data 102.

In some implementations, data received by the computer 106 is a form of non-genomic data. For example, information can be received by the computer 106. The information can then be processed in one or more stages. In some cases, the information can be processed by one or more modules such as the hash operation module 108, the occurrence counter module 114, or the hash table generation module 120.

In some implementations, data related to the information received by the computer 106 is used to alter one or more processing operations. For example, the received information may be used to alter the operation of any operation module of the computer 106 such as the hash operation module 108, the occurrence counter module 114, or the hash table generation module 120. For example, the computer 106 can receive information. The computer 106 can extract one or more items from the received information. The computer 106 can determine, based on the extracted one or more items, a particular processing method to be applied to the received information. In some cases, the particular processing method may include one or more processing modules, where the one or more processing modules are adjusted with parameter changes or operational changes to process data in a particular way based on the extracted one or more items.

For example, in generating a hash table related to genomic data, the computer 106 may receive genomic data. The computer 106 may extract one or more items (e.g., one or more k-mers of a particular length ki) from the received genomic data. The computer 106 may then alter the operating method of one or more modules based on the extracted data. For example, the computer 106 may alter the occurrence counter module 114 by changing a threshold value representing an integer number k that indicates a number of base calls or nucleotides in the k-mer. Items that do not meet the threshold value set by the computer 106 may be filtered out.

In some implementations, the k-mer set 104 can include a plurality of k-mer nucleic acid sequences, each of length k, which are derived from the genomic data 102, which can include a reference sequence. In some implementations, the computer 106 can receive the k-mer set 104 via a direct connection (e.g., USB connection, USB-C connection, or the like) or via one or more network connections (e.g., LAN, WAN, Ethernet, WiFi, cellular network, the Internet, or the like). In some implementations, the computer 106 can be a nucleic acid sequencing device and the nucleic acid sequencing device can receive, obtain, or otherwise access the genomic data 102 and generate the k-mer set 104.

Accordingly, in some implementations, the software-accelerated genomic mapping and aligning of the present disclosure can be implemented on a sequencing device such as a next generation DNA sequencing device to perform secondary analysis operations such as mapping and aligning genomic data reads on the sequencing device. In other implementations, the software-accelerated genomic data mapping and aligning of the present disclosure can be implemented on another computer other than the sequencing device that obtains genomic data, generates a k-mer set 104, and performs one or more of the other operations described herein below using the k-mer set 104, or a portion thereof.

In stage B, the hash operation module 108 receives the k-mer set 104. The computer 106 of the example shown in FIG. 1 may be communicably connected to the hash operation module 108. The hash operation module 108 can perform one or more operations based on the k-mer set 104. For example, as shown in FIG. 1, each k-mer of the k-mer set 104 can be used to generate a corresponding hash value. The hash value may be any value. In the example of FIG. 1, the hash value is determined to be a value between 0 and $2^{64}-1$.

The hash operation module 108 can generate computed hash values 112. The computed hash values 112 can be processed in order to filter the received k-mer set 104. For example, the hash operation module 108 can use the computed hash values 112 to determine a subset of the k-mer set 104 shown in the example of FIG. 1 as a second k-mer set 110. In some implementations, a first filtering stage can be implementing by determining a subset of the k-mer set 104 using a modulo function. In some implementations, the computed hash values 112 can be generated by the hash operation module 108 corresponding to a predetermined mapping. For example, as shown in FIG. 1, the mapping may be defined as:

$$H_{k\text{-}mer}\text{:kmer} \mapsto [0;2^{64}-1] \qquad (1)$$

Equation 1 is an example of a hash function that can be used by the hash operation module 108 to compute one or more hash values. Equation 1 describes a mapping of a given k-mer of the k-mer set 104 to a corresponding hash value, in this case the hash value is a value between 0 and $2^{64}-1$ and the hash values can be represented by a 64 bit unsigned integer. In some implementations, other mappings or hash functions are used resulting in different hash values. For example, instead of a 64 bit unsigned integer, a 32 bit signed integer may be used. The present disclosure does not limit the form of mapping or hash function used by the hash function module 108. In some cases, the type of hash function may change depending on data received by the computer 106 or data received by the hash operation module 108.

In processing the k-mer set 104, the hash operation module 108 of FIG. 1 can perform one or more operations. In some implementations, the one or more operations can include computing one or more values. In the example of FIG. 1, the hash operation module 108 can compute a hash value for each k-mer of the k-mer set 104. An example of a hash value calculation performed by the hash operation module 108 is shown in Equation 2.

$$H_{k\text{-}mer}(\text{GTTA} \ldots \text{AC}) = 98778 \ldots 789 \qquad (2)$$

Equation 2 is directed to the example of FIG. 1 and the first k-mer of the k-mer set 104, "GTTA ... AC". In Equation 1, the hash operation module 108 computes the hash value 98778 ... 789 based on the hash function $H_{k\text{-}mer}$ and the k-mer GTTA ... AC where the value 98778 ... 789 represents a value between 1 and $2^{64}-1$ and "GTTA . . . AC" represents a genomic data read, or a portion thereof, defined by a k-mer of the k-mer set 104. The hash function $H_{k\text{-}mer}$ can be any suitable hash function as will be understood by one skilled in the art. The hash function $H_{k\text{-}mer}$ can be configured to map a k-mer of the k-mer set 104 to a certain value within a value range as shown in Equation 1.

The hash operation module 108 can perform further operations based on the k-mer set 104. In the example of FIG. 1, the hash operation module 108 can generate the hash value 98778 . . . 789 corresponding to the k-mer GTTA . . . AC. The hash operation module can compute another value based on the hash value as shown in Equation 3.

$$H_{k\text{-}mer}(\text{GTTA} \ldots \text{AC}) \text{modulo seedModValue} = 98778 \ldots 789 \text{ modulo } 8 = 0 \quad (3)$$

Equation 3 shows computation performed by the hash operation module 108 in the example of FIG. 1. The hash value 98778 . . . 789 corresponding to the k-mer GTTA . . . AC is used to compute a second value. The second value is the result of a modulo operation performed on the hash value 98778 . . . 789. The modulo operation is based on the hash value 98778 . . . 789 and a seedModValue. The seedModValue is either predetermined or determined by the hash operation module 108 or the computer 106 responsive to the k-mer set 104. In the example of FIG. 1, the seedModValue is the integer 8. However, the seedModValue may be any integer number. The seedModValue can be optimized or altered based on an optimization operation or other use case. The seedModValue may be any value depending on implementation.

The hash operation module 108 can generate the second k-mer set 110 based on the computed hash values 112 and the seedModValue. Any suitable rule sets can be applied by the hash operation module 108 to generate the second k-mer set 110. In the example of FIG. 1, the hash operation module 108 can generate the hash value 98778 . . . 789 and perform a modulo operation on the hash value 98778 . . . 789 based on the seedModValue that is equal to 8 in the current example. The modulo operation and result is shown in Equation 3. The result is 0. According to internal rules of the hash operation module 108 shown in FIG. 1, the result of 0 causes the hash operation module 108 to include the corresponding k-mer, in this case, k-mer GTTA . . . AC, in the second k-mer set 110. The k-mer GTTA . . . AC is not crossed out showing that the second k-mer set 110 includes the k-mer GTTA . . . AC.

The hash operation module 108 can also compute a hash value for other k-mers included in the k-mer set 104. The k-mer TATA . . . CG of the k-mer set 104 is used to compute a hash value 65432 . . . 611 of the computed hash values 112. As discussed above, the hash operation module 108 can perform a modulo operation using the seedModValue. In this case, the hash operation module 108 can compute a value of 2. The hash operation module 108 can determine to not include the k-mer TATA . . . CG in the second k-mer set 110 based on the value of the result of the modulo operation applied to the hash value 65432 . . . 611. In the example of FIG. 1, the k-mer TATA . . . CG is crossed out showing that the k-mer TATA . . . CG is not included in the second k-mer set 110.

The hash operation module 108 can compute corresponding hash values for other k-mers of the k-mer set 104. As discussed above, the hash operation module can filter the k-mers of the k-mer set 104 by performing operations on the k-mers of the k-mer set 104. In the example of FIG. 1, the hash operation module 108 can compute a hash value and a result of a modulo operation applied to the computed hash value. Based on the result of the modulo operation, the hash operation module 108 can filter k-mers of the k-mer set 104 and generate the second k-mer set 110. In some implementations, the filtered set of k-mers, such as the second k-mer set 110, will include each of the k-mers for which the hash operation (e.g., a modulo 8 operation or other suitable operation) yielded a calculation result of 0. That is, each of the k-mers that have a hash value that, when operated on by the hash operation module 108, yielded a result different than 0 are filtered out. The second k-mer set 110 is a subset of the k-mer set 104. However, the present disclose is not limited to use of a modulo 8 operation or use of a modulo operation on hash values at all in order to perform the filter operations. Various other filtering techniques may be used as will be understood by one skilled in the art.

In some implementations, filtering can include various computer programs run on a computer. For example, as shown in algorithm 1 below, a computer program can initiate one or more system variables and perform one or more operations based on the one or more system variables. In some cases, 'if' statements or other conditional coding operations can be used to determine items that are to be filtered.

Algorithm 1 Seed selection on reference genome

```
1:  SeedLength = 16
2:  SeedModValue = 8
3:  MaxSeedOccurrence = 20
4:  for each overlapping seed s on the reference genome do
5:     if H_seed(s) modulo SeedModValue = 0 then
6:        if N B_occ(s) < MaxSeedOccurrence then
7:           Insert seed s with position of its first occurrence on the genome in the hash table
```

In some implementations, a filtering technique may be used to extract one or more items from genomic data. For example, an extraction module can extract k-mers at predetermined intervals within a parent data store, e.g., a genomic sequence, a data structure including genomic data, or other form of ordered data store. In some implementations, the extraction module can locate a first k-mer within a sequence. The extraction module can then locate a second k-mer within the sequence where the second k-mer is separated from the first k-mer by a predetermined number of nucleotides s. In this case, s can be an integer greater than 0. A third k-mer may be determined using the same interval s as used for finding the second k-mer based on the first k-mer. The operation may continue until a predetermined ending condition is met, e.g., a predetermined number of k-mers are found or when the extraction module has reached the end of the sequence. In some implementations, the above example may be used to filter other forms of data stores. For example, a fixed interval can be used to extract one or more elements from the k-mer set 104 thereby filtering the k-mer set 104.

An extraction module can locate a first k-mer within a data structure such as the k-mer set 104 and then locate a second k-mer within the k-mer set 104 where the second k-mer is separated from the first k-mer by a predetermined number of indices i. In a data store without indices, counts or other values may be used to denote a fixed separation between adjacent extracted elements.

In some implementations, an item within an ordered data set can be chosen based on one or more conditions of a filtering method that uses a predetermined interval. For example, as discussed above, an ordered data set can be filtered based on one or more items extracted from the ordered data set. Adjacent items of the one or more items extracted from the ordered data set may be separated from each other by a predetermined interval. In some implementations, a first value is chosen so as to select one or more items of the ordered data set based on the predetermined interval. In some cases, the first value is chosen in a similar manner or to equivalent specifications across at least two or more input data sets to produce similar filtered sets for the two or more input data sets.

In some implementations, a hash method of filtering is used to improve performance of a system such as the system 100 of FIG. 1. For example, a hash function can be applied by the hash operation module 108 to k-mers of a reference genome and k-mers of a genomic read. By filtering the k-mers based on a constant hash function and modulo operation across both the reference genome and the genomic read, the same types of k-mers can be selected from the reference genome and the genomic read by the hash operation module 108. By using the hash method of filtering, memory usage as well as processing time can be reduced based on filtering the k-mer set that needs to be indexed, querying only a subset of k-mers within the filtering operation, and the similar selections between the reference genome and the genomic read as mentioned above.

In stage C, the occurrence counter module 114 can use the second k-mer set 110 to apply a second filter stage to the k-mer set 104. In some implementations, the occurrence counter module 114 can implement a second filtering stage by computing a number of genome occurrences 118 for one or more k-mers of the second k-mer set 110. The number of genome occurrences 118 for each k-mer can include, for example, a number of times that the particular k-mer appears in a reference genome (also referred to as a reference sequence). In some implementations, the occurrence counter module 114 can compare the number of occurrences for each k-mer to a threshold value. In the example of FIG. 1, the threshold value is defined as 20. In other implementations, the threshold value may be any applicable value.

Though a second filtering stage is described herein for determining a number of occurrences for a k-mer in a reference sequence, the second filtering stage of the present disclosure is not so limited. Instead, other filters can also be used for the second filtering stage. Moreover, in some implementations, the present disclosure may employ zero filtering stages, one filtering stage, or two or more filtering stages. Instead of the filtering stages being a limiting feature of the present disclosure, the filtering stages are customizable during the design of a software-accelerated genomic data mapping algorithm to achieve a third k-mer set 116 that is suitable for use in generating a hash table 124 for a particular implementation.

In the example of FIG. 1, the occurrence counter module 114 determines that the k-mer GTTA . . . AC occurs 15 times within the genomic data 102 such as a reference sequence. The k-mer TATA . . . CG is not computed, because the k-mer TATA . . . CG has been filtered out during the first filtering stage based on the modulo operation. The k-mer CCGA . . . GT occurs 23 times within the genomic data 102 and the k-mer AAGT . . . AT occurs 11 times within the genomic data 102.

Based on the number of genome occurrences 118, the occurrence counter module 114 can determine each k-mer seed of the second k-mer set 110 to include in the third k-mer set 116. Each entry of the number of genome occurrences 118 is compared to a threshold value MaxSeedOccurrence. The MaxSeedOccurrence value can have an integer value such as 20. If an item of the number of genome occurrences 118 is above or equal to the threshold, the corresponding k-mer is not included in the third k-mer set 116. If an item of the number of genome occurrences 118 is below the threshold, the corresponding k-mer is included in the third k-mer set 116. The k-mer GTTA . . . AC and the k-mer AAGT . . . AT are both included in the third k-mer set 116 as the corresponding occurrence numbers, 15 and 11, both satisfy the threshold MaxSeedOccurrence. Other k-mers of the second k-mer set 110 not shown may also be included in the third k-mer set 116. The k-mer CCGA . . . GT is not included in the third k-mer set 116 as the corresponding occurrence number, 23, does not satisfy the threshold MaxSeedOccurrence.

As described above, at least a portion of the operations performed by the hash operation module 108 and the occurrence counter module 114 can be described as respective filtering stages applied to the received genomic data 102 such as reference sequence data. In some implementations, the filtering can be used for a number of reasons including, for example, to decrease memory usage and decrease computation time of the overall operation corresponding to the received data. In some implementations, other forms of filtering may be used to generate a subset of received data. For example, an algorithm, such as a random algorithm can generate a list of indices corresponding to indices used in received data. If an index is included in the output of the random algorithm, the corresponding value of the received data can either be included or not included in the subset of data. In this way, a subset of the received data can be generated. Other methods involving random number generation may also be used as will be apparent to one skilled in the art.

In some implementations, filtering can be used to filter received genomic data 102 based on relevant properties of the data. For example, as shown in FIG. 1, the second k-mer set 110 can be filtered by the occurrence counter module 114 based on occurrences of each k-mer within the genomic data 102. In some implementations, this can be a relevant filter, because k-mers with high occurrence counts tend to be more likely to generate candidate alignment positions that will yield alignment with low quality scores. As one of the motivations of the present specification is to generate good candidate alignments, k-mers with high occurrences, defined in the example of FIG. 1 as occurrences over 20, are not included in a generated subset that will be included in the generation of a hash table.

In stage D of FIG. 1, the hash table generation module 120 can generate a hash table based on the third k-mer set 116. In the example of FIG. 1, the hash table generation module 120 generates a hash table 124 represented as a one-dimensional array consisting of data blocks that include signature values and location values. The hash table generation module 120 only records k-mers that have passed the filtering steps of the hash operation module 108 and the occurrence counter module 114 into the hash table 124. For example, k-mer GTTA . . . AC and k-mer AAGT . . . AT are recorded into the hash table 124, while the k-mer TATA . . . CG and the k-mer CCGA . . . GT are not.

The value corresponding to a k-mer recorded in the hash table 124 can include a position of the given k-mer within the genomic data 102. In some implementations, only the first occurrence of the k-mer within the genomic data is included in the value data section of the hash table for the given k-mer. In such implementations, the other positions are then discarded. A conceptual example of the value generated corresponding to the k-mer GTTA . . . AC is shown in item 126. A reference 126b, is shown corresponding to the k-mer GTTA . . . AC at a first occurrence 126a. In the example of FIG. 1, the reference 126b corresponds to the genomic data 102. The noted portion of the reference 126b includes the sequence corresponding to the k-mer GTTA . . . AC, namely, a sequence of nucleotides in the sequence represented by "GTTA . . . AC". The sequence "GTTA . . . AC" may occur at other positions on the reference 126b, but only the first occurrence of the sequence "GTTA . . . AC" is stored as a value in the hash table 124 corresponding to the k-mer GTTA . . . AC.

In some implementations, inserting items into the hash table 124 can include various computer programs run on a computer. For example, as shown in algorithm 2 below, a computer program can initiate one or more system variables and perform one or more operations based on the one or more system variables. In some cases, 'if' statements or other conditional coding operations can be used to determine items that are to be filtered.

---

Algorithm 2 Insertion of pair (seed, position) in the hash table $\mathcal{HT}$

---

1:    index = $H_{tab}$(seed)
2:    if $\mathcal{HT}$ [index].sig = $H_{sig}$(seed) then
3:       Compute new index with linear probing
4:    $\mathcal{HT}$ [index] ← ($H_{sig}$(seed), position)

---

The signature corresponding to the k-mer GTTA . . . AC is computed using a hash function. In the example of FIG. 1, the hash function maps a given k-mer to a range of 0 to 255. As shown in item 128, the k-mer GTTA . . . AC is used as input for the hash function H_sig. The hash table generation module 120 uses the hash function H_sig to map the k-mer value to the value 248. The value 248 is then used as the key corresponding to the k-mer GTTA . . . AC within the hash table 124.

By mapping the k-mer value to a number on the range of 0 to 255, the hash table generation module 120 is able to decrease the amount of data stored on the hash table 124. For a k-mer that is 16 nucleotides long, 32 bits may be required to render corresponding data within a data structure. By mapping the k-mer value to another value, for example, a value between 0 and 255 as shown in item, the required space is reduced. For example, if the k-mer GTTA . . . AC includes 16 nucleotides and the resulting signature from the mapping operation is the number 248 that can be expressed with 8 bits, the memory footprint for the data stored within the hash table 124 is reduced by a quarter.

In some implementations, other methods can be used to reduce a corresponding key to reduce a hash table size. For example, instead of mapping a given value of received data using a hash function, the trailing x number of digits of a value can be used to represent a location that can be expressed within a data structure. Other similar methods of compressing the data of the hash table will be apparent to one skilled in the art.

In some implementations, the hash table 124 can be an array of a specified length. For example, the hash table 124 can include a single array containing N continuous cells. The hash table 124 can also use a linear probing technique for collision resolution. In some implementations, configurations corresponding to an array configuration of the hash table 124 can result in a single cache miss and improved performance over other similar methods. By improving the performance of the hash table 124, a system, such as the system 300, for mapping a read to a reference genome can be improved so that the system can generate mapping results with higher accuracy and in a shorter amount of time compared to other mapping methods.

The index corresponding to the k-mer GTTA . . . AC can be computed using a hash function. In the example of FIG. 1, a hash function H_tab is used where H_tab is not identical to the H_sig hash function used to generate the signature. In some implementations, the H_tab hash function can also use the k-mer as input but generates outputs to a different range of values. The range of values output by the H_tab hash function can correspond to the number of indices available within the hash table 124. In some implementations, the hash table 124 can include on the order of $2^{28}$ cells that may be indexed. As shown in item 130, the H_tab hash function can operate on the k-mer GTTA . . . AC and output a value of 268435456 corresponding to an index within the hash table 124. The value and signature, shown in items 126 and 128 respectively, can be stored at index location 268435456 within the hash table 124.

When querying a cell in a hash table, the signature of the cell may be used to identify the cell holding the particular k-mer. If a cell with the particular signature is found, associated values, index, or other parameters may be returned. In some implementations, multiple different k-mers may correspond to the same signature. For example, the hash table 124 may include a first k-mer corresponding to a first signature and a second k-mer corresponding to a second signature where values representing the first signature and the second signature are equivalent. In such implementations, querying the hash table to find the first signature and corresponding information of the first k-mer may result in the hash table 124 outputting information related to the second k-mer.

The hash table 124 can be designed for low memory usage and for fast queries. For example, the hash table 124 of FIG. 1 is designed to store a list of key value pairs with the key being something used to identify the k-mer and the value being the k-mer position within the genomic data 102. In some implementations, one position within the genomic data 102 is stored per k-mer. In some implementations, other positions are stored. For example, every other position, e.g., odd numbered positions or the like, of a given k-mer within the genomic data 102 can be stored in the hash table corresponding to the given k-mer.

Figure 3:
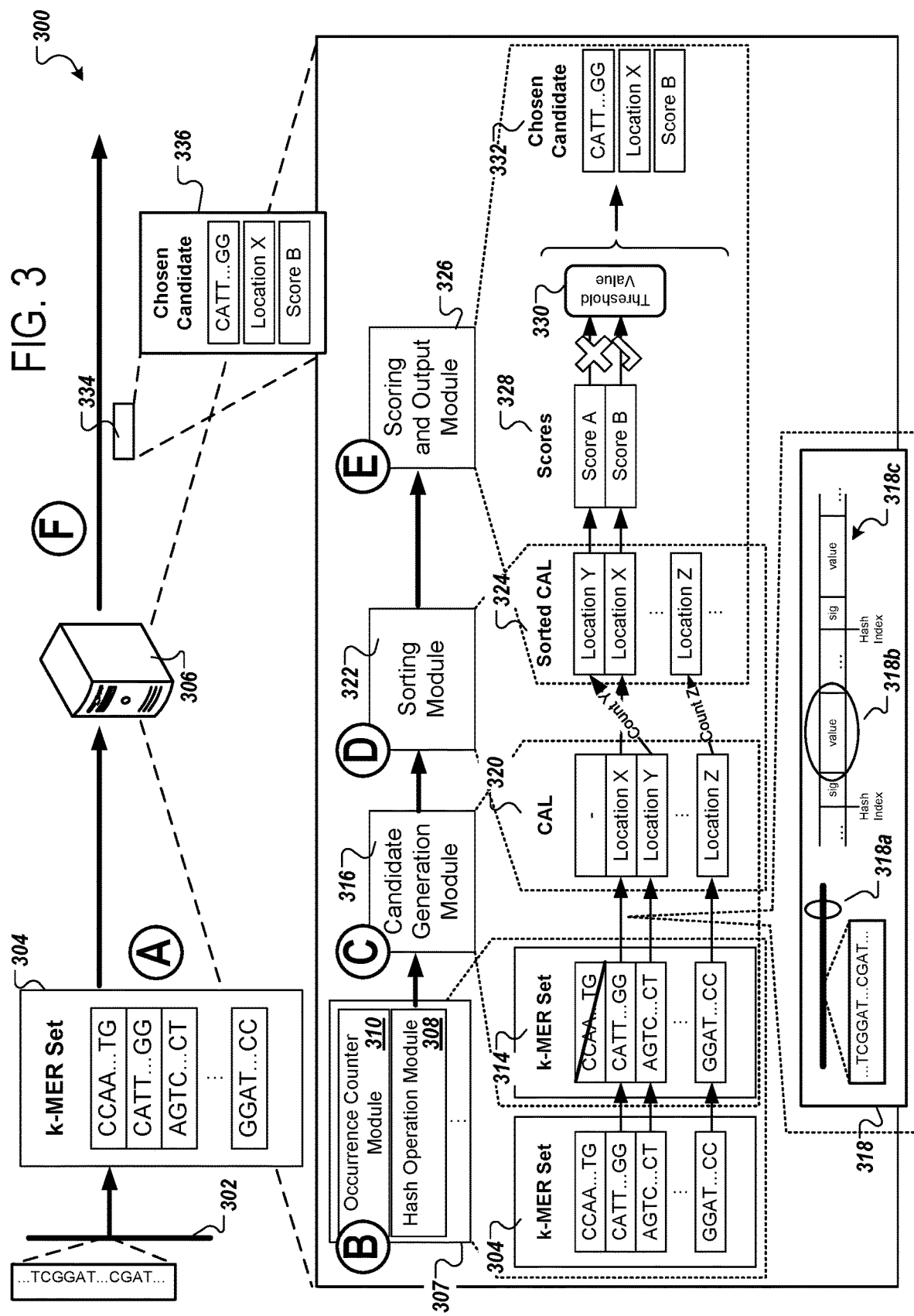
FIG. 3 is a diagram showing an example of a system for using a hash table for software accelerated genomic read mapping.

In some implementations, the hash table 124 can be stored within memory of the computer 106 for future use at stage E. For example, the hash table 124 may be used in an application of candidate alignment location and evaluation as shown in FIG. 3. In other implementations, the hash table 124 can be sent by the computer 106 to a device communicably connected to the computer 106 at stage E. Such a device can be communicably connected to the computer 106 via one or more direct connections or via one or more network connections such as over the Internet. In some implementations, the hash table 124 can be generated by the computer 106 and stored within a data storage entity such as thumb drive, hard drive, or other form of electronic data storage at stage E. In some cases, the data storage entity is connected to a processor that can query or edit the hash table 124.

In some implementations, the computer 106 can send other data related to the hash table 124 to another process or device. For example, instead of sending the hash table 124, the computer 106 can send computation systems, algorithms, or the like to another process or device. In some implementations, the computer 106 can store data, including the hash table 124 or the data related to the hash table 124 on a memory device such that the memory device may be used to read data from the hash table 124 or generate a hash table similar to the hash table 124 based on the data related to the hash table 124. For example, the computer 106 can send data related to one or more modules, such as the hash operation module 108, the occurrence counter module 114, or the hash table generation module 120 to another process or device. The data related to the one or more modules may be used by another system or the system 100 to generate one or more other hash tables based on the data related to the one or more modules.

In some implementations, the computer 106 can generate a hash table installation package that includes software instructions for installing the hash table 124 on another computer and the genomic data 102. In other implementations, the computer 106 may provide only the software instructions, as the receiving computer may already have a copy of the genomic data. In some implementations, the hash table installation package can include software instructions that, when executed, perform the operations described by the process 200 of FIG. 2. The other computer can receive the hash table installation package, execute the hash table installation package, and install the hash table 124. The other computer can then perform software accelerated genomic read mapping using the processes described herein with respect to FIGS. 3 and 4.

In some implementations, the hash table 124 can use open addressing. For example, hash collisions can be resolved through searching alternate locations in the array of the hash table 124 until either the target cell is found or an unused cell is found. A cell may be a location within the hash table 124 in which data can be stored. In some implementations, linear probing or other form of probing such as quadratic probing, double hashing program or the like, can be used to determine an index for storing data corresponding to a given k-mer. In some implementations, linear probing can be used for improved cache locality which may translate into higher performance than implementations that do not utilize linear probing. In the example of FIG. 1, both the key and value are stored together in the array of the hash table 124. By storing the key and value together, cache locality can be further increased.

In some implementations, a form of probing can be used to generate new indices. For example, in an implementation that uses linear probing, if a first k-mer maps to a particular index based on the hash function H_tab, and that index includes an occupied cell with the same signature as the signature computed by the hash function H_sig on the first k-mer, then a new index may be computed. In the case of linear probing, and index value can be increased by 1 until a signature value at a given index is not equal to the signature value corresponding to the output of H_sig operating on the first k-mer. Of course, any other suitable probing may be used in a given implementation.

In some implementations, the hash table 124 can include cells of a predetermined memory size. For example, the hash table 124 can include memory cells containing 5 bytes of memory. In some implementations, 1 byte is devoted to a signature value and 4 bytes is devoted to the location value as shown in item 128 and item 126 respectively. However, other memory layouts can be used depending on implementation.

In some implementations, a signature can be generated and stored in the hash table 124. For example, a signature based on a given k-mer, such as the k-mer GTTA . . . AC can be generated and stored in the hash table 124. In some implementations, the signature generated can be smaller in terms of data usage than a binary representation of the k-mer itself. In this way, memory usage may be further reduced and performance may be increased. In the example of FIG. 1, the signature corresponding to k-mer GTTA . . . AC is generated using a hash function as shown in item 128. In this case, the hash function H_sig is used.

In some implementations, other forms of a hash table are generated by the hash table generation module 120. For example, instead of a one dimensional vector represented as a single array, the hash table generation module 120 can generate a multi-dimensional vector using multiple arrays. In some cases, the form of hash table generated by the hash table generation module 120 can be determined based on the received data that in the example of FIG. 1 is the k-mer set 104. For example, the hash table generation module 120 can change the form of a hash table from a one dimensional array with certain properties to a multi-dimensional vector, a table, a one dimensional array, or another form of hashed indexed database each with different properties. However, implementations that use a one-dimensional vector represented as a single array provide particular technological benefits such as ensuring that hash queries can be resolved with no more than a single cache miss.

In some implementations, the computer 106 can be configured to perform the actions attributed to the hash operation module 108, the occurrence counter module 114, and the hash table generation module 120. In other implementations, one or more of the hash operation module 108, the occurrence counter module 114, and the hash table generation module 120 can be performed on one or more devices communicably connected to the computer 106. In some implementations, the one or more devices communicably connected to the computer 106 can include other computers, servers, nucleic acid sequencers, or other devices.

In some implementations, one or more processing steps can be performed before or after the processing steps as shown in the example of FIG. 1. For example, the k-mer set 104, after being received by the computer 106, may be pre-processed to change the format of the k-mer set 104 before the operations of the hash operations module 108 occur.

In some implementations, one or more of the operations shown in the example of FIG. 1 may be removed without straying from the scope of the present specification. For example, in some cases, the hash operation module 108 can send output data directly to the hash table generation module 120 without any operations performed by the occurrence counter module 114. Various other modifications may be considered by one skilled in the art.

As another example, in some implementations, the system 100 can be implemented without serial generation of complete and different k-mer sets 110, 116. Instead, the processes of the hash operation module 108, the occurrence counter module 114, and the hash table generation module 120 can be implemented in a pipelined manner. For example, the hash operation module 108 can compute the hash value 98778 . . . 789 corresponding to the k-mer GTTA . . . AC and execute a first filtering stage by computing a result of the hash value 98778 . . . 789 modulo seedModValue. If the result of the modulo operation is 0, the occurrence counter module 114 can directly receive the k-mer GTTA . . . AC, determine a number of genome occurrences corresponding to the k-mer GTTA . . . AC, and execute a second filter stage based on the number of genome occurrences corresponding to the k-mer GTTA . . . AC. The hash table generation module 120 can, in a similar manner, receive the k-mer GTTA . . . AC and perform its operations, as described herein, once the k-mer GTTA . . . AC passes the second filtering stage of the occurrence counter module 114. Accordingly, some implementations, separate sets of received data such as k-mer data need not be generated. Instead, the modules of the present disclosure can be configured to operate in a pipelined manner, with a subsequent processing module operating on the output of a previous processing module after the output of the previous processing module is generated. This pipelined operation can result in faster execution of the software-accelerated genomic data mapping algorithm.

Figure 2:
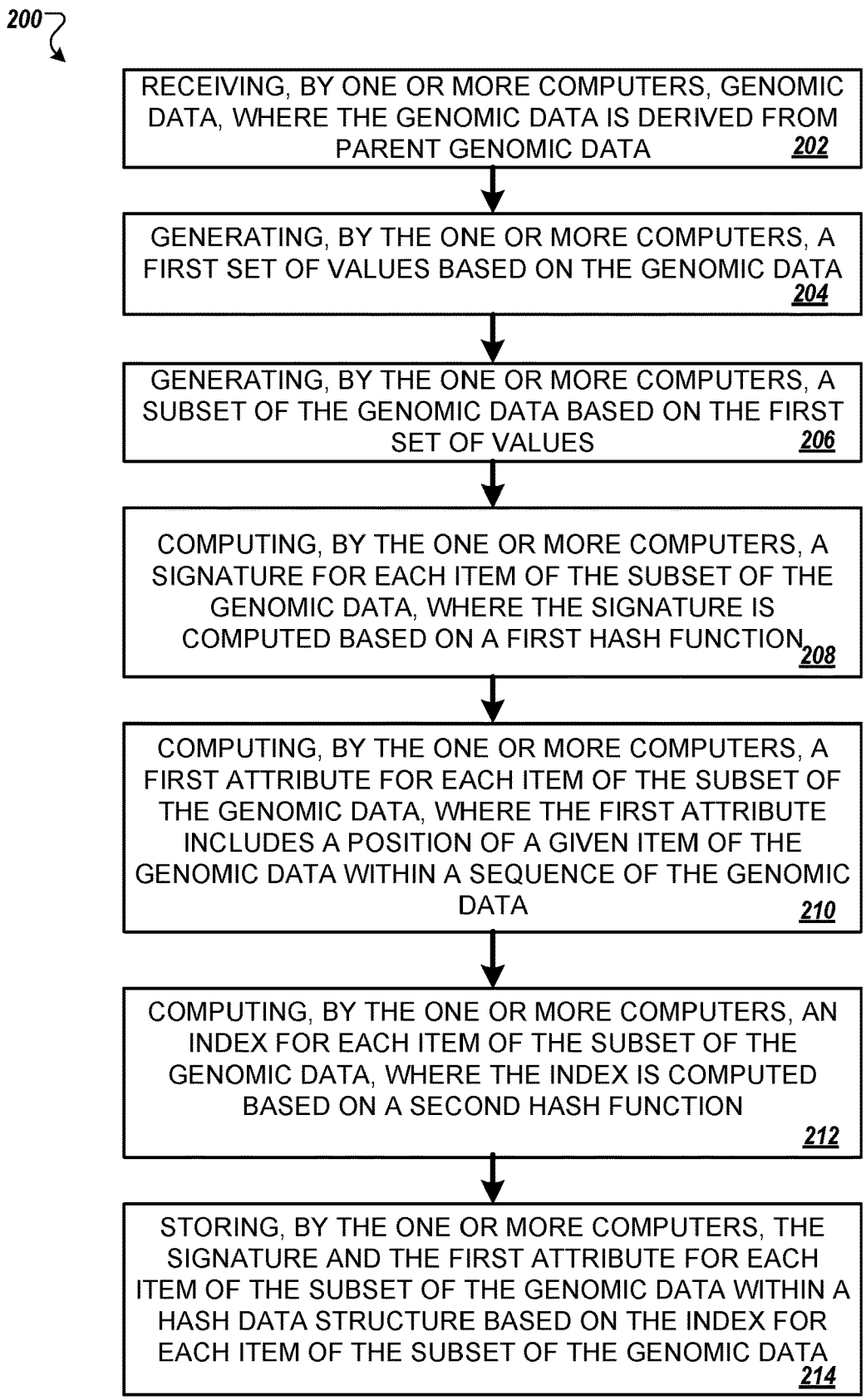
FIG. 2 is a flow diagram illustrating an example of a process for generating a hash table for software accelerated genomic read mapping.

FIG. 2 is a flow diagram illustrating an example of a process 200 for generating a hash table for software accelerated genomic read mapping. The process 200 can be performed by one or more electronic systems, for example, the system 100 of FIG. 1.

The system 100 can begin execution of the process 200 receiving, by one or more computers, genomic data, where the genomic data is derived from parent genomic data (202). In some implementations, the genomic data is parsed into one or more k-mers. The k-mers can be a data structure that includes one or more fields, each field can represent one or more of k nucleic acid nucleotides or bases.

The process 200 includes generating, by the one or more computers, a first set of values based on the genomic data (204). In some implementations, the first set of values is based on a hash value, a hash function, or both. For example, the first set of values can include a first value based on a first k-mer of the genomic data. The first value can be the result of a modulo operator operating on a hash value where the hash value can be generated from the first k-mer of the genomic data by a hash function. In some implementations, other operations or methods may be used to generate the first set of values. For example, the first set of values can include an occurrence count of a given k-mer of the genomic data.

The process 200 includes generating, by the one or more computers, a subset of the genomic data based on the first set of values (206). For example, the first set of values can be a form of filtering data used to filter the genomic data that includes a first number of k-mers to generate a subset of the genomic data where the subset of the genomic data includes fewer k-mers based on filtering informed by the first set of values.

The process 200 includes computing, by the one or more computers, a signature for each item of the subset of the genomic data, where the signature is computed based on a first hash function (208). In some implementations, a hash function can be predetermined. The predetermined hash function can then be used to generate the signature based on a given item of the subset of the genomic data. In some implementations, the signature is a genomic signature. In some implementations, the signature is stored with data related to a given k-mer and is used to identify the data related to the given k-mer as data corresponding to the given k-mer as shown in FIG. 1.

The process 200 includes computing, by the one or more computers, a first attribute for each item of the subset of the genomic data, where the first attribute includes a position of a given item of the genomic data within a sequence of the genomic data (210). In this context, an item can include a k-mer seed. In some implementations, the first attribute only includes the first occurrence of the given item of the genomic data within the sequence. For example, the given item of the genomic data may occur more than once within the sequence. In order to reduce the amount of memory required to store genomic data in a data structure such as a hash table, a system implementing the process 200, such as the system 100, can store only the first occurrence and not store any subsequent occurrence of the given item. In some implementations, a genomic data representation is parsed by a computer in a given direction. The given direction determines which occurrence is selected as the "first" occurrence.

The process 200 includes computing, by the one or more computers, an index for each item of the subset of the genomic data, where the index is computed based on a second hash function (212). In some implementations, the second hash function is predetermined by the system 100. In some implementations, the second hash function is used to generate an index to locate data corresponding to a given k-mer within a hash table such as the hash table 124. The index can point to a specific location within memory associated with the hash table 124.

The process 200 includes storing, by the one or more computers, the signature and the first attribute for each item of the subset of the genomic data within a hash data structure based on the index for each item of the subset of the genomic data (214). For example, as shown in FIG. 1, the system 100 can store a signature of k-mer GTTA . . . AC as shown in item 128 and a value corresponding to the k-mer GTTA . . . AC as shown in item 126. In some implementations, the hash table 124 is a single array storing signatures and values within elements along the single dimension of the single array. In some implementations, the signature used within the hash table 124 is stored as a single byte and the value stored as the first attribute, such as location of the k-mer associated with the signature, is stored as a 4 byte memory unit. In some implementations, a given k-mer of the subset of the genomic data is stored within the hash table 124 in a 5 byte memory unit such that each item of the subset of the genomic data occupies 5 bytes of memory within a cell of the hash table 124.

FIG. 3 is a diagram showing an example of a system 300 for using a hash table for software accelerated genomic read mapping. The system 300 includes a computer 306, a filter module 307 that includes, in this example, a hash operation module 308 and an occurrence counter module 310, a candidate generation module 316, a sorting module 322 and a scoring and output module 326. In some implementations, the computer 106 of FIG. 1 is communicably connected to the computer 306. In some implementations, the computer 306 obtains the hash table 124 or related data based on processes performed by the computer 106. In some implementations, the computer 306 and the computer 106 refer to the same device. In some implementations, either the computer 106, the computer 306, or both, can be a nucleic acid sequencer.

Figure 4:
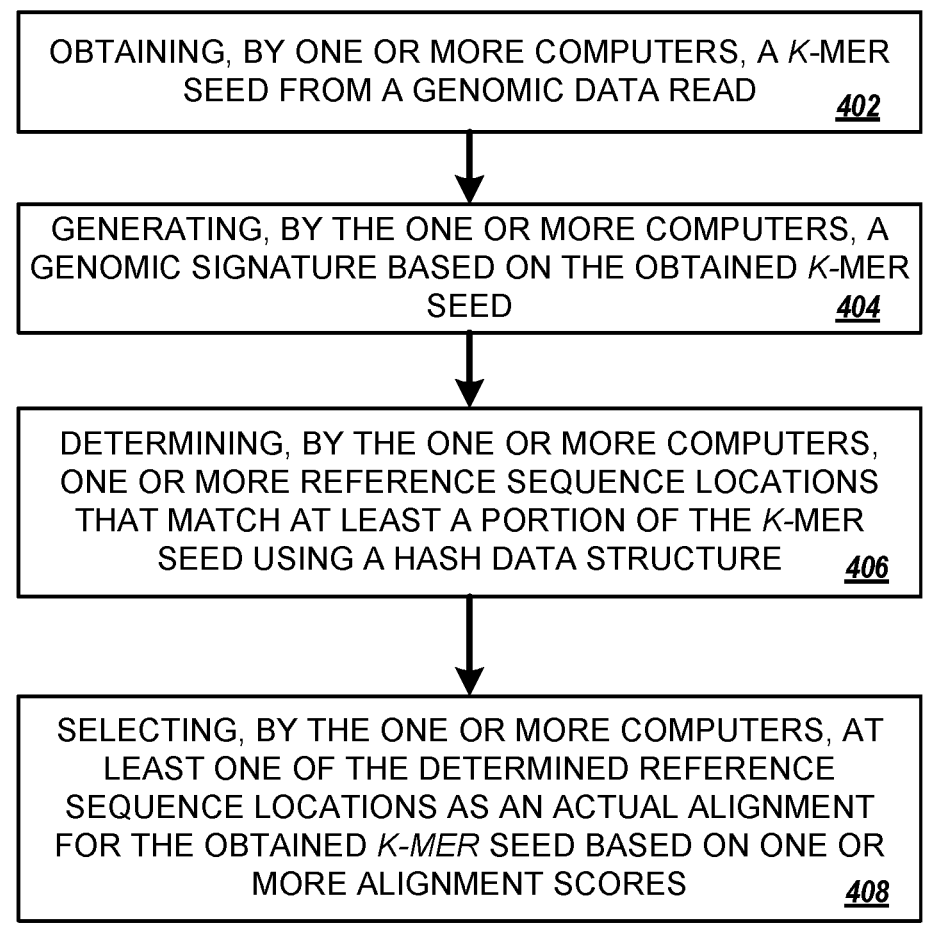
FIG. 4 is a flow diagram illustrating an example of a process for generating a hash table for software accelerated genomic read mapping.

In the example of FIG. 3, the genomic data read 302 is a nucleic acid sequence read. The computer 306 can receive the genomic data read 302 and map the received genomic data read 302 to a reference genome stored within a hash table generated using the one or more of the systems, processes, or both, described with reference to FIGS. 1 and 2. For example, the hash table 124 generated in FIG. 1 may be used to store a reference genome. A subsequent read of genomic data may then be mapped to the reference genome of the hash table 124 using the process as shown in FIG. 3 or 4.

In stage A of FIG. 3, the computer 306 can obtain the k-mer set 304 that is generated based on the genomic data read 302. Similar to FIG. 1, the k-mer set 304 includes one or more nucleotide sequences that are expressed at least once within the genomic data read 302. The computer 306 can receive the k-mer set 304 for processing. In the example of FIG. 3, the k-mer set 304 can represent k-mers identified in a read of the genomic data read 302. The genomic data read 302 can be mapped to a reference genome using a hash table such as the hash table 124 generated in FIG. 1.

In stage B of FIG. 3, the hash operation module 308 and the occurrence counter module 310 can perform operations similar to the operations discussed in reference to the hash operation module 108 and the occurrence counter module 114 of FIG. 1. For example, the hash operation module 308 and the occurrence counter module 310 perform filtering on the k-mer set 304 while the hash operation module 108 and the occurrence counter module 114 perform filtering on the k-mer set 104. As discussed within the specification, although genomic data is described in detail, other forms of received data may be received by entities such as the computer 106 and the computer 306. The other forms of received data can be similarly processed by related modules. Processing steps may be altered based on the other forms of received data. The computer 306 or the computer 106, as discussed, may alter operations depending on the form, type, or value of the data that the computer 306 or the computer 106 receive.

In some implementations, other forms of filtering can be used. For example, instead of having both the hash operation module 308 and the occurrence counter module 310 operate on the k-mer set 304, the hash operation module 308 may perform the sole filter process of generating hash values and determining based on the hash values a subset of the k-mer set 304 referred to here as a second k-mer set 314. In some cases, another form of filtering is used instead of, or in addition to, the hash operation module 308 or the occurrence counter module 310.

In some implementations, filtering can include various computer programs run on a computer. For example, as shown in algorithm 3 below, a computer program can initiate one or more system variables and perform one or more operations based on the one or more system variables. In some cases, 'if' statements or other conditional coding operations can be used to determine items that are to be filtered.

representing a number of occurrences in which each k-mer of the k-mer set 304 occurs within the genomic data read 302. The hash values can be generated and processed by the hash operation module 308 such that, based on the hash value of a given k-mer, the hash operation module 308 either includes the k-mer or does not include the k-mer in further processes in the system 300. The occurrences are generated and processed by the occurrence counter module 310 such that, based on the number of occurrences of a given k-mer, the occurrence counter module 310 either includes the k-mer or does not include the k-mer in further processes in the system 300. The occurrence values generated by the occurrence counter module 310 can be a number of times the given k-mer, that is the nucleotide sequence of the k-mer, appears within the larger sequence of the genomic data read 302.

In some implementations, the hash operation module 308 can use a modulo operation similar to the modulo operation discussed in reference to FIG. 1. The hash operation module 308 may compute a given hash value modulo a seedModValue. In some cases, the seedModValue is equal to an integer such as 8. The present specification is not limited to any specific number. The value of seedModValue may be altered based on an optimization operations or other various parameters.

In some implementations, certain value ranges for one or more variables discussed herein may be advantageous over other possible value ranges. For example, the MaxSeedOccurrence may be increased to allow more k-mers to be indexed within a given hash table such as the hash table 124. However, increasing the MaxSeedOccurrence can potentially increase the memory usage and size of the hash table 124 which may, in part, increase processing time. A very low value may lead to a smaller hash table with fewer data points to match a read based on the hash table, thereby potentially reducing the accuracy of results obtained based on the hash table. Various other trade-offs and effects may depend on one or more related variables. For example, one or more variables including seed length that indicates a length of a given k-mer or seed, read length that indicates a length of a given read, the particular reference genome used, number of positions stored within a hash table or related variables may be altered based on a processing state, user preference, performance, or other condition.

In reference to the seedModValue used in the examples of FIG. 1 and FIG. 3, in some implementations, the value associated with the seedModValue may be reduced to increase the size of a resulting filtered set of k-mers or other items. For example, in an extreme case, the seedModValue can be reduced to the value of 1 in which case the modulo operation discussed herein will equal 0. In implementations where 0 is a value that determines a given k-mer is included in the filtered set, a modulo value of 1 means that the entire set of k-mers or other items will be used as the final filtered

---

Algorithm 3 Seed selection on read

1: SeedLength = 16
2: SeedModValue = 8
3: for each overlapping seed s in the read do
4:     if $H_{seed}(s)$ modulo SeedModValue = 0 then
5:         Query seed s in the hash table to get its position on the reference genome

---

Similar to the filtering process discussed above, a k-mer set 304 that includes one or more k-mers can be used to compute one or more hash values and one or more values set. In some implementations, a larger number may be used for the seedModValue. For example, in an extreme case, the seedModValue can be increased to a value of 100. A resulting filtering operation with a high seedModValue value will leave fewer items in the final filtering result. In some cases, this can result in a greater number of unmapped reads. For read lengths around 100 nucleotides, values of seedModValue above 100 will potentially lead to too many reads being unmapped and thus will generally not result in effective processing. However, for longer reads, on the order of 1000 nucleotides, higher values of seedModValue may potentially be more advantageous.

Both MaxSeedOccurrence and seedModValue can have a direct impact on hash table size. Memory usage for a given hash table can be defined as the number of seeds or k-mers kept after filtering multiplied by both the size of each cell in the hash table and a loading factor used to generate enough cells for a given amount of values. Given the case of 1 byte signatures and 4 byte values resulting in 5 bytes per cell, each cell in a hash table such as the hash table 124 may occupy 5 bytes of memory. For illustration purposes, consider the example of the human genome. The human genome includes about 3 billion nucleotides. In some cases, from the human genome, about 3 billion k-mers may be derived depending on one or more variables including seed length. Without any filtering, such as the hash or occurrence filtering discussed in the examples of FIG. 1 and FIG. 3, the filtered set of k-mers associated with the human genome will be equal to the initial set of k-mers associated with the human genome, that is, about 3 billion. If the k-mers are stored corresponding to cells of 5 bytes, and the hash table is generated based on a loading factor of 2, the human genome may be stored in a hash table of 30 gigabytes. With filtering, e.g., with hash filtering using a seedModValue of 8 and occurrence filtering using a MaxSeedOccurrence of 20, the same human genome may be stored in approximately 1.4 gigabytes. Changing the value of seedModValue to 4 would roughly double the memory usage. In some implementations, values may be chosen based on desired memory usage for a given application. The most advantageous values may be chosen based on one or more optimization processes that include automatically varying the values of one or more values including seedModValue, MaxSeedOccurrence, seed length, read length, sequencing error rate, or any other related parameters.

In some implementations, the occurrence counter module 310 can use an occurrence threshold similar to the occurrence counter module 114 of FIG. 1. For example, the occurrence counter module 310 can compare each occurrence value computed for each k-mer of the k-mer set 304 to an occurrence threshold. Based on a comparison between the occurrence value and the occurrence threshold, the occurrence counter module 310 either includes the k-mer or does not include the k-mer in further processes using the system 300 corresponding to a given occurrence value.

In the example of FIG. 3, the k-mer set 304 can be filtered to produce the second k-mer set 314. The second k-mer set 314 is a subset of the k-mer set 304. In some implementations, the second k-mer set 314 is generated based on other filtering techniques. For example, instead of processing by the hash operation module 308 and the occurrence counter module 310, the system 300 may include a random number generator and use the output of the random number generator to generate a subset of the k-mer set 304. Other filtering techniques known in the art can also be used to decrease the number of items within a given data set such that a subsequent data set includes fewer items than an initial data set. In some implementations, filtering techniques discussed in reference to FIG. 1 may also be used such as random algorithms or fixed stride length indexing.

In stage C of FIG. 3, the candidate generation module 316 generates candidate alignment locations 320. In some cases, candidate alignment locations may be referred to as reference sequence locations. The candidate alignment locations 320 include information corresponding to where, within a reference genome, data corresponding to the read represented by the genomic data read 302 occurs. In some implementations, the system 300 can use k-mers corresponding to the genomic data read 302 within the k-mer set 304 to determine, based on the positions of the k-mers within the k-mer set 304, where the read represented by the genomic data read 302 matches to the reference genome. The reference genome may be stored in a hash table as shown in FIG. 1. The hash table may be used by the system 300 to determine corresponding positions for the one or more k-mers of the k-mer set 304.

The candidate generation module 316 can generate the candidate alignment locations 320 based on the k-mers of the second k-mer set 314. For example, as shown in FIG. 3, the k-mer CATT . . . GG corresponds to a location "Location X" of the genomic data read 302 on the reference genome. Item 318 shows the process of generating the candidate alignment location corresponding to the k-mer CATT . . . GG. After the k-mer CATT . . . GG passes one or more filtering steps, the k-mer CATT . . . GG is queried in a hash table 318c. In some implementations, the hash table 318c is equivalent to the hash table 124 of FIG. 1. A value 318b, corresponding to the reference genome position corresponding to the k-mer CATT . . . GG can be obtained by the candidate generation module 316. The candidate generation module 316 also obtains a location of the k-mer CATT . . . GG within the genomic data read 302 as shown in item 318a. Based on the location of the k-mer CATT . . . GG within the genomic data read 302, shown in item 318a, and the location of the k-mer CATT . . . GG within the reference genome, shown in item 318b corresponding to the hash table 318c, the candidate generation module 316 can determine the location "Location X" corresponding to the mapping of the genomic data read 302 mapped on the reference genome corresponding to the k-mer CATT . . . GG.

In some implementations, the candidate generation module 316 can compute one or more locations based on one or more obtained locations. For example, for the k-mer CATT . . . GG, the candidate generation module 316 can obtain the location of the k-mer CATT . . . GG within the genomic data read 302, shown in item 318a, and the location of the k-mer CATT . . . GG within the reference genome, shown in item 318b corresponding to the hash table 318c, and compute the location "Location X" based on the two locations. For example, in implementations where locations of matching sequences are stored as the start of a matching sequence between two or more reads, the candidate generation module 316 can generate the location "Location X" based on subtracting the position of the k-mer CATT . . . GG within the genomic data read 302 from the position of the k-mer CATT . . . GG within the hash table 318c corresponding to the reference genome. The candidate generation module 316 can generate locations for the k-mers CATT . . . GG, AGTC . . . CT, and GGAT . . . CC using similar methods.

In stage D of FIG. 3, the sorting module 322 can sort the candidate alignment locations 320. In general, any suitable sorting technique may be used. In the example of FIG. 3, the sorting module 322 can sort the candidate alignment locations 320 based on computed counts. The computed counts represent a number of supporting k-mers for a given candidate alignment location of the candidate alignment locations 320. For example, one or more of the locations in the candidate alignment locations 320 may be duplicates indicating that two or more k-mers of the second k-mer set 314 correspond to the same alignment of the genomic data read 302 on the reference genome represented by the hash table 318c. If two k-mers correspond to the same alignment, the count of that alignment is 2. In the example of FIG. 3, the count for the location "Location X" is count X, the count for the location "Location Y" is count Y, and the count for the location "Location Z" is count Z. The alignments can be sorted in decreasing order such that the count Y that is greater than the count X and the count Z results in the Location Y being stored above Location X and Location Z. Similarly, count X is greater than count X resulting in Location X being stored above Location Z. In the example of FIG. 3, the alignment locations can be sorted in decreasing order but other possible sorting orders are contemplated herein.

Sorting the alignments based on decreasing order may be used in order to optimize the alignments processing steps. For example, alignments with a greater number of supporting k-mers tend to have fewer mismatches than alignments with a fewer number of supporting k-mers. Each k-mer may be investigated to determine a number of mismatches before choosing a final alignment. By processing the alignments more likely to pass a set of criteria first, the system 300 can speed up processing of the alignments.

In stage E, the scoring and output module 326 can obtain the first location of a sorted candidate alignment list 324 corresponding to the Location Y. The Location Y is scored based on the reference genome corresponding to the hash table 318c. In the example of FIG. 3, the scoring and output module 326 can compute a number of mismatches between genomic data, such as the genomic data read 302, corresponding to the k-mer AGTC . . . CT associated with the Location Y and the reference genomic data corresponding to the hash table 318c where the reference genomic data is used to generate the hash table 318c. A mismatch may refer to a nucleotide of the genomic data read 302 not matching a nucleotide of the reference genomic data. For example, at a given location along matched sequences, one sequence may correspond to the nucleotide A while the other sequence may correspond to the nucleotide G. Such a mismatch may be calculated by the scoring and output module 326.

The scoring and output module 326 can generate a total number of mismatches corresponding to the alignment Location Y and generates a score A where the score A represents at least a number of mismatches. In some cases other parameters or values may be used to generate scores 328 including the score A. In the example of FIG. 3, the scoring and output module 326 can compare the score A to a threshold value 330. The threshold value 330 may, in general, be any suitable value. In the example of FIG. 3, the threshold value 330 is equal to the value 4 where 4 represents a number of mismatches. In some implementations, other values may be used. For example, optimization processes may be used to determine another suitable value for the threshold value 330. The scoring and output module 326 can determine, based on comparing the score A to the threshold value 330 that the score A does not satisfy the threshold and therefore the Location Y is not chosen. The scoring and output module 326 can then process one or more other locations.

The scoring and output module 326 can generate a total number of mismatches corresponding to the alignment Location X and generate a score B where the score B represents at least a number of mismatches. In the example of FIG. 3, the scoring and output module 326 can compare the score B to the threshold value 330. The scoring and output module 326 can determine based on the comparison of the score B to the threshold value 330 that the score B satisfies the threshold value 330. Based on determining that the score B satisfies the threshold value 330, the scoring and output module 326 can output a chosen candidate 332. The chosen candidate 332 may include data representing the k-mer CATT . . . GG, the Location X, or the score B.

In some implementations, no scores satisfy the criteria. In this case, one score may be chosen from among the scores 328 based on a given criteria. For example, the given criteria may include comparing one or more of the scores 328 to determine a minimum score representing an alignment with the least amount of mismatches. The location corresponding to the lowest score can then be output as the chosen candidate.

In stage F, the computer 306 can obtain the chosen candidate 332 and sends data 334 that represents the chosen candidate 332 to another entity or process. In some cases, the computer 306 can send the data 334 over a communication network to another entity or device. For example, another device may send a request for a chosen candidate related to the genomic data read 302. The computer 306 can then send the chosen candidate 332 to the other device.

FIG. 4 is a flow diagram illustrating an example of a process 400 for generating a hash table for software accelerated genomic read mapping. The process 400 may be performed by one or more electronic systems, for example, the system 300 of FIG. 3.

The process 400 includes obtaining, by one or more computers, a k-mer seed from a genomic data read (402). In some implementations, the k-mer seed is a representation of a sequence of nucleotides based on a longer sequence of nucleotides associated with the genomic data read. In some implementations, the genomic data read is the result of a read analysis operation performed on a computer or hardware accelerated device.

The process 400 includes generating, by the one or more computers, a genomic signature based on the obtained k-mer seed (404). In some implementations, the candidate generation module 316 of FIG. 3 is used, in part, to generate a signature of the obtained k-mer seed. In some implementations, the signature of the obtained k-mer seed is generated based on a hash function. For example, a hash function can operate on a representation of the obtained k-mer seed. The hash function can generate a result that may be used as a genomic signature. In some implementations, one or more intermediary processing steps can be employed before or after the hash function generates a result. For example, the hash function can generate a result and a second operation can be applied to the result in order to generate the genomic signature.

The process 400 includes determining, by the one or more computers, one or more reference sequence locations that match at least a portion of the k-mer seed using a hash data structure (406). In some implementations, the hash data structure includes N data cells that include a first portion storing a predetermined genomic signature and a second portion storing one or more references sequence locations that match at least a portion of a k-mer seed from which the predetermined genomic signature was derived. In some implementations, the predetermined genomic signature occupies 1 byte of memory storage. In some implementations, the hash data structure is generated similar to the process of generating the hash table 124 shown in FIG. 1.

The process 400 includes selecting, by the one or more computers, at least one of the determined reference sequence locations as an actual alignment for the obtained k-mer seed based on one or more alignment scores (408). In some implementations, one or more locations are determined and a method of scoring the one or more locations is used in order to determine the actual alignment for the obtained k-mer seed based on the one or more alignment scores. For example, a number of mismatches for a given alignment can be computed where a number of mismatches can include one or more nucleotides of a read not matching one or more nucleotides of a reference nucleotide sequence. The mismatches may be computed based on representations of the one or more nucleotides of the read and representations of the one or more nucleotides of the reference nucleotide sequence and a comparison between the two based on a given candidate starting location of the read relative to the reference nucleotide sequence.

Figure 5:
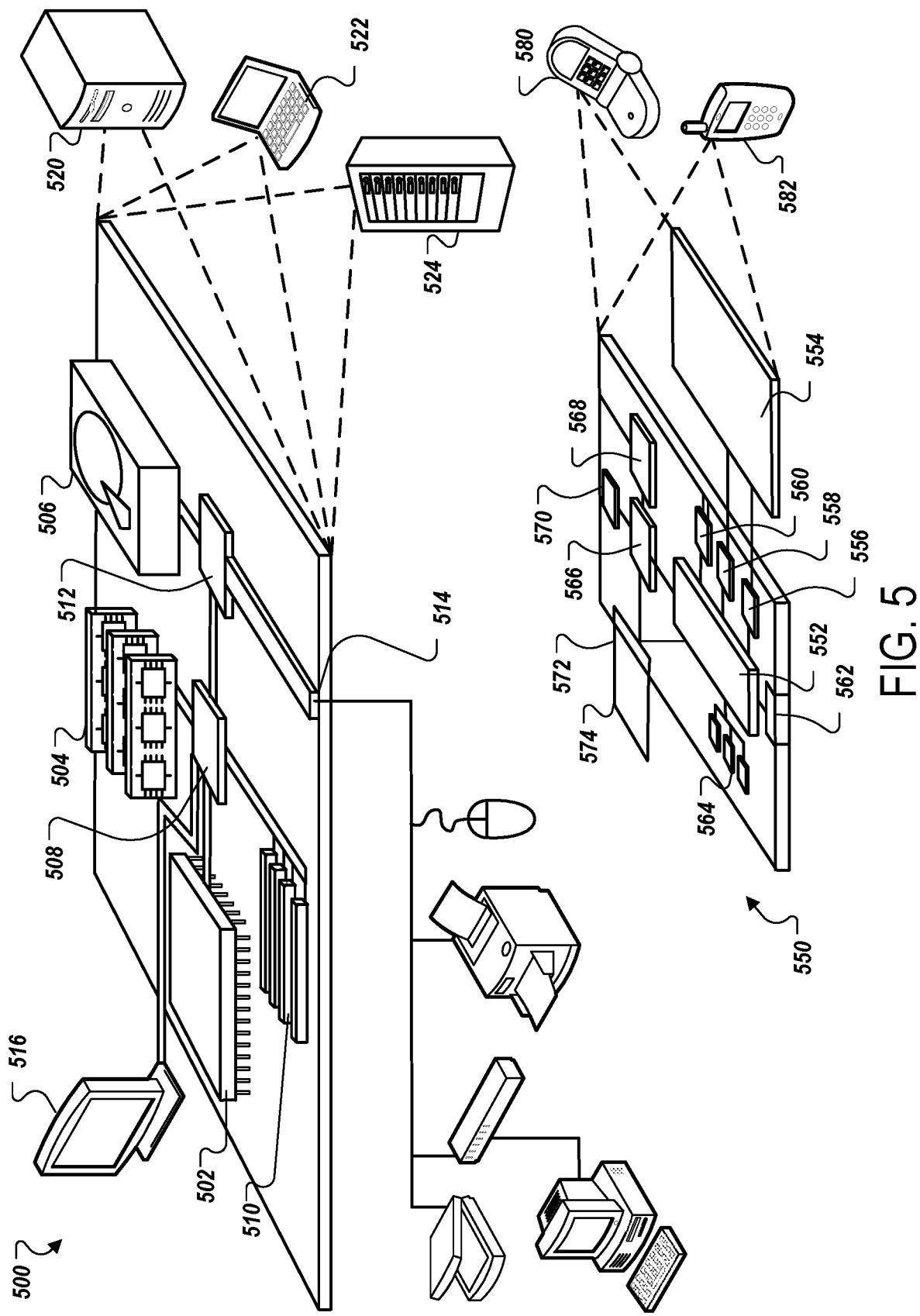
FIG. 5 is a diagram of computer system including components that can be used to implement a system for generating a hash table for software accelerated genomic read mapping.

FIG. 5 is a diagram of computer system 500 including components that can be used to implement a system for generating a hash table for software accelerated genomic read mapping.

Computing device 500 is intended to represent various forms of digital computers, such as laptops, desktops, workstations, personal digital assistants, servers, blade servers, mainframes, and other appropriate computers. Computing device 550 is intended to represent various forms of mobile devices, such as personal digital assistants, cellular telephones, smartphones, and other similar computing devices. Additionally, computing device 500 or 550 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be examples only, and are not meant to limit implementations of the inventions described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and can be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses can be used, as appropriate, along with multiple memories and types of memory. Also, multiple computing devices 500 can be connected, with each device providing portions of the necessary operations, e.g., as a server bank, a group of blade servers, or a multi-processor system.

The memory 504 stores information within the computing device 500. In one implementation, the memory 504 is a volatile memory unit or units. In another implementation, the memory 504 is a non-volatile memory unit or units. The memory 504 can also be another form of computer-readable medium, such as a magnetic or optical disk.

The storage device 506 is capable of providing mass storage for the computing device 500. In one implementation, the storage device 506 can be or contain a computer-readable medium, such as a floppy disk device, a hard disk device, an optical disk device, or a tape device, a flash memory or other similar solid-state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 504, the storage device 506, or memory on processor 502.

The high-speed controller 508 manages bandwidth-intensive operations for the computing device 500, while the low speed controller 512 manages lower bandwidth intensive operations. Such allocation of functions is only an example. In one implementation, the high-speed controller 508 is coupled to memory 504, display 516, e.g., through a graphics processor or accelerator, and to high-speed expansion ports 510, which can accept various expansion cards (not shown). In the implementation, low-speed controller 512 is coupled to storage device 506 and low-speed expansion port 514. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.

The computing device 500 can be implemented in a number of different forms, as shown in the figure. For example, it can be implemented as a standard server 520, or multiple times in a group of such servers. It can also be implemented as part of a rack server system 524. In addition, it can be implemented in a personal computer such as a laptop computer 522. Alternatively, components from computing device 500 can be combined with other components in a mobile device (not shown), such as device 550. Each of such devices can contain one or more of computing device 500, 550, and an entire system can be made up of multiple computing devices 500, 550 communicating with each other.

Computing device 550 includes a processor 552, memory 564, and an input/output device such as a display 554, a communication interface 566, and a transceiver 568, among other components. The device 550 can also be provided with a storage device, such as a micro-drive or other device, to provide additional storage. Each of the components 550, 552, 564, 554, 566, and 568, are interconnected using various buses, and several of the components can be mounted on a common motherboard or in other manners as appropriate.

The processor 552 can execute instructions within the computing device 550, including instructions stored in the memory 564. The processor can be implemented as a chipset of chips that include separate and multiple analog and digital processors. Additionally, the processor can be implemented using any of a number of architectures. For example, the processor 510 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 550, such as control of user interfaces, applications run by device 550, and wireless communication by device 550.

Processor 552 can communicate with a user through control interface 558 and display interface 556 coupled to a display 554. The display 554 can be, for example, a TFT (Thin-Film-Transistor Liquid Crystal Display) display or an OLED (Organic Light Emitting Diode) display, or other appropriate display technology. The display interface 556 can comprise appropriate circuitry for driving the display 554 to present graphical and other information to a user. The control interface 558 can receive commands from a user and convert them for submission to the processor 552. In addition, an external interface 562 can be provided in communication with processor 552, so as to enable near area communication of device 550 with other devices. External interface 562 can provide, for example, for wired communication in some implementations, or for wireless communication in other implementations, and multiple interfaces can also be used.

The memory 564 stores information within the computing device 550. The memory 564 can be implemented as one or more of a computer-readable medium or media, a volatile memory unit or units, or a non-volatile memory unit or units. Expansion memory 574 can also be provided and connected to device 550 through expansion interface 572, which can include, for example, a SIMM (Single In Line Memory Module) card interface. Such expansion memory 574 can provide extra storage space for device 550, or can also store applications or other information for device 550. Specifically, expansion memory 574 can include instructions to carry out or supplement the processes described above, and can also include secure information. Thus, for example, expansion memory 574 can be provided as a security module for device 550, and can be programmed with instructions that permit secure use of device 550. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552 that can be received, for example, over transceiver 568 or external interface 562.

Device 550 can communicate wirelessly through communication interface 566, which can include digital signal processing circuitry where necessary. Communication interface 566 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 568. In addition, short-range communication can occur, such as using a Bluetooth, Wi-Fi, or other such transceiver (not shown). In addition, GPS (Global Positioning System) receiver module 570 can provide additional navigation- and location-related wireless data to device 550, which can be used as appropriate by applications running on device 550.

Device 550 can also communicate audibly using audio codec 560, which can receive spoken information from a user and convert it to usable digital information. Audio codec 560 can likewise generate audible sound for a user, such as through a speaker, e.g., in a handset of device 550. Such sound can include sound from voice telephone calls, can include recorded sound, e.g., voice messages, music files, etc. and can also include sound generated by applications operating on device 550.

The computing device 550 can be implemented in a number of different forms, as shown in the figure. For example, it can be implemented as a cellular telephone 580. It can also be implemented as part of a smartphone 582, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Other Embodiments

Particular embodiments of the invention have been described. Other embodiments are within the scope of the following claims. For example, the steps recited in the claims can be performed in a different order and still achieve desirable results.

What is claimed is:

1. A method for generating a hash table for software-accelerated genomic data read mapping, the method comprising:
   receiving, by one or more computers, genomic data, wherein the genomic data is derived from parent genomic data;
   generating, by one or more computers, a first set of values based on the genomic data;
   generating, by one or more computers, a subset of the genomic data based on the first set of values;
   computing, by one or more computers, a signature for each k-mer of the subset of the genomic data, wherein the signature is computed based on a first hash function;
   computing, by one or more computers, a first attribute for each k-mer of the subset of the genomic data, wherein the first attribute comprises a position of a given k-mer of the genomic data within a sequence of the genomic data;
   computing, by one or more computers, an index for each k-mer of the subset of the genomic data, wherein the index is computed based on a second hash function; and
   storing, by one or more computers, the signature and the first attribute for each k-mer of the subset of the genomic data within a hash data structure based on the index for each k-mer of the subset of the genomic data.

2. The method of claim 1, wherein each k-mer of the subset of the genomic data is a k-mer comprising k letters representing a string of one or more nucleotides.

3. The method of claim 1, wherein the first set of values comprises a representation of a number of times that a given k-mer of the genomic data occurs within the parent genomic data.

4. The method of claim 1, wherein the first set of values comprises a representation of a hash value computed based on a corresponding k-mer of the genomic data.

5. The method of claim 1, wherein a memory allocation size used to store the signature for a given k-mer of the subset is smaller than a memory allocation size used to store the given k-mer.

6. The method of claim 1, the method further comprising:
   sending, by one or more computers, data corresponding to the hash data structure as a data package to a first device.

7. A system for generating a hash table for software-accelerated genomic data read mapping, the system comprising:
   one or more computers; and
   one or more memories storing instructions that, when executed by the one or more computers, cause the one or more computers to perform operations, the operations comprising:
      receiving, by the one or more computers, genomic data, wherein the genomic data is derived from parent genomic data;
      generating, by the one or more computers, a first set of values based on the genomic data;
      generating, by the one or more computers, a subset of the genomic data based on the first set of values;
      computing, by the one or more computers, a signature for each k-mer of the subset of the genomic data, wherein the signature is computed based on a first hash function;
      computing, by the one or more computers, a first attribute for each k-mer of the subset of the genomic data, wherein the first attribute comprises a position of a given k-mer of the genomic data within a sequence of the genomic data;
      computing, by the one or more computers, an index for each k-mer of the subset of the genomic data, wherein the index is computed based on a second hash function; and
      storing, by the one or more computers, the signature and the first attribute for each k-mer of the subset of the genomic data within a hash data structure based on the index for each k-mer of the subset of the genomic data.

8. The system of claim 7, wherein each k-mer of the subset of the genomic data is a k-mer comprising k letters representing a string of one or more nucleotides.

9. The system of claim 7, wherein the first set of values comprises a representation of a number of times that a given k-mer of the genomic data occurs within the parent genomic data.

10. The system of claim 7, wherein the first set of values comprises a representation of a hash value computed based on a corresponding k-mer of the genomic data.

11. The system of claim 7, wherein a memory allocation size used to store the signature for a given k-mer of the subset is smaller than a memory allocation size used to store the given k-mer.

12. The system of claim 7, the operations further comprising:
sending, by the one or more computers, data corresponding to the hash data structure as a data package to a first device.

13. The system of claim 12, wherein the first device is a memory storage device.

14. The system of claim 12, wherein a second device reads the data corresponding to the hash data structure from the first device, and wherein the second device performs a series of operations to generate a second hash data structure based on the data corresponding to the hash data structure.

15. A computer-readable medium storing instructions that, when executed by one or more computers, cause the one or more computers to perform operations for generating a hash table for software-accelerated genomic data read mapping, the operations comprising:
receiving genomic data, wherein the genomic data is derived from parent genomic data;
generating a first set of values based on the genomic data;
generating a subset of the genomic data based on the first set of values;
computing a signature for each k-mer of the subset of the genomic data, wherein the signature is computed based on a first hash function;
computing a first attribute for each k-mer of the subset of the genomic data, wherein the first attribute comprises a position of a given k-mer of the genomic data within a sequence of the genomic data;
computing an index for each k-mer of the subset of the genomic data, wherein the index is computed based on a second hash function; and
storing the signature and the first attribute for each k-mer of the subset of the genomic data within a hash data structure based on the index for each k-mer of the subset of the genomic data.

16. The computer-readable medium of claim 15, wherein each k-mer of the subset of the genomic data is a k-mer comprising k letters representing a string of one or more nucleotides.

17. The computer-readable medium of claim 15, wherein the first set of values comprises a representation of a number of times that a given k-mer of the genomic data occurs within the parent genomic data.

18. The computer-readable medium of claim 15, wherein the first set of values comprises a representation of a hash value computed based on a corresponding k-mer of the genomic data.

19. The computer-readable medium of claim 15, wherein a memory allocation size used to store the signature for a given k-mer of the subset is smaller than a memory allocation size used to store the given k-mer.

20. The computer-readable medium of claim 15, the operations further comprising:
sending data corresponding to the hash data structure as a data package to a first device.

* * * * *